(12) United States Patent
Lattimore

(10) Patent No.: US 10,595,944 B2
(45) Date of Patent: Mar. 24, 2020

(54) SURGICAL ROBOTIC CART WITH SELECTIVE WHEEL ALIGNMENT

(71) Applicant: Covidien LP, Mansfield, MA (US)

(72) Inventor: James Lattimore, Fairport, NY (US)

(73) Assignee: COVIDIEN LP, Mansfield, MA (US)

( * ) Notice: Subject to any disclaimer, the term of this patent is extended or adjusted under 35 U.S.C. 154(b) by 40 days.

(21) Appl. No.: 15/765,544

(22) PCT Filed: Oct. 5, 2016

(86) PCT No.: PCT/US2016/055393
§ 371 (c)(1),
(2) Date: Apr. 3, 2018

(87) PCT Pub. No.: WO2017/062391
PCT Pub. Date: Apr. 13, 2017

(65) Prior Publication Data
US 2018/0280095 A1    Oct. 4, 2018

Related U.S. Application Data

(60) Provisional application No. 62/239,393, filed on Oct. 9, 2015.

(51) Int. Cl.
| | |
|---|---|
| *A61B 34/00* | (2016.01) |
| *A61B 34/30* | (2016.01) |
| *A61B 50/13* | (2016.01) |
| *A61B 90/50* | (2016.01) |
| *A61B 50/26* | (2016.01) |
| *B60B 33/02* | (2006.01) |
| *B62B 3/12* | (2006.01) |
| *B60B 33/00* | (2006.01) |

(52) U.S. Cl.
CPC .............. *A61B 34/30* (2016.02); *A61B 50/13* (2016.02); *A61B 50/26* (2016.02); *A61B 90/50* (2016.02); *B60B 33/02* (2013.01); *B62B 3/12* (2013.01); *B60B 33/0042* (2013.01); *B60B 33/0049* (2013.01); *B60B 33/0068* (2013.01); *B60B 33/0073* (2013.01); *B60B 2200/26* (2013.01); *B62B 2301/04632* (2013.01)

(58) Field of Classification Search
CPC ......... A61B 34/30; A61B 50/10; A61B 50/13; B60B 33/00; B60B 33/0068; B60B 1/006
See application file for complete search history.

(56) References Cited

U.S. PATENT DOCUMENTS

| | | |
|---|---|---|
| 1,804,541 A | 5/1931 | Perin |
| 2,925,887 A | 2/1960 | Gibson |
| 8,448,729 B2 | 5/2013 | Schena et al. |

(Continued)

OTHER PUBLICATIONS

International Search Report & Written Opinion corresponding to Int'l Appln. No. PCT/US2016/055393 dated Jan. 17, 2017.

(Continued)

*Primary Examiner* — Hau V Phan

(57) ABSTRACT

A mobile surgical robotic cart assembly includes a vertical column supporting a robotic arm thereon, a base, and a plurality of casters each having wheels and each being attached to the base thereby allowing the surgical robotic assembly to move. Each of the plurality of casters has a wheel alignment assembly configured to lock each of the respective wheels in a plurality of orientations.

19 Claims, 4 Drawing Sheets

(56) References Cited

U.S. PATENT DOCUMENTS

| | | | |
|---|---|---|---|
| 9,370,617 B2* | 6/2016 | Chepurny | A61G 12/008 |
| 10,123,842 B2* | 11/2018 | Iceman | B25J 5/007 |
| 2007/0056141 A1 | 3/2007 | Armano et al. | |
| 2007/0129634 A1* | 6/2007 | Hickey | A61B 8/00 |
| | | | 600/439 |
| 2009/0019670 A1 | 1/2009 | Tsai | |
| 2009/0276977 A1* | 11/2009 | Liao | B60B 33/0018 |
| | | | 16/35 R |
| 2010/0107360 A1* | 5/2010 | Shih | B60B 1/006 |
| | | | 16/21 |
| 2011/0152844 A1* | 6/2011 | Charles | A61B 50/10 |
| | | | 606/1 |
| 2012/0317752 A1 | 12/2012 | Dayt | |
| 2013/0292521 A1* | 11/2013 | Chepurny | A61G 12/008 |
| | | | 248/97 |
| 2014/0186792 A1* | 7/2014 | Rose | A61C 1/0015 |
| | | | 433/29 |
| 2014/0238784 A1 | 8/2014 | Yeo | |
| 2015/0040352 A1* | 2/2015 | Tsai | B60B 33/0086 |
| | | | 16/35 R |
| 2015/0230869 A1 | 8/2015 | Shim et al. | |
| 2015/0239291 A1 | 8/2015 | Jie | |
| 2016/0221392 A1* | 8/2016 | Steenson | B60B 33/0057 |
| 2017/0065355 A1* | 3/2017 | Ross | A61B 34/30 |
| 2017/0190212 A1* | 7/2017 | Horch | B60B 33/00 |

OTHER PUBLICATIONS

Extended European Search Report corresponding to counterpart Patent Application EP 16854184.5 dated May 10, 2019.

* cited by examiner

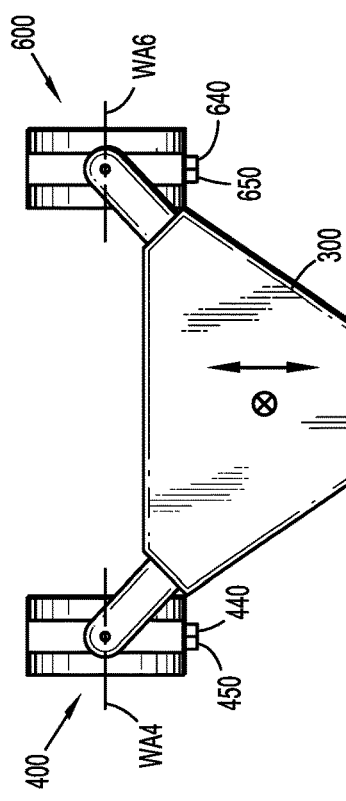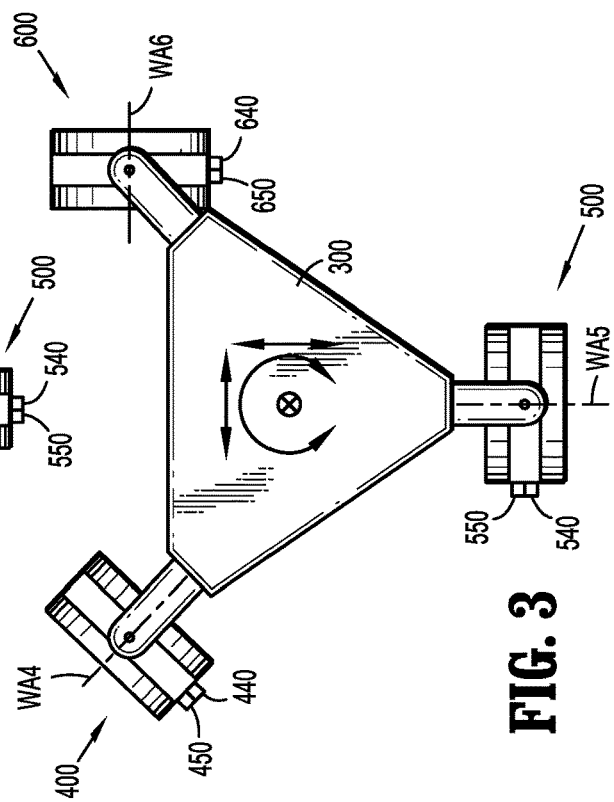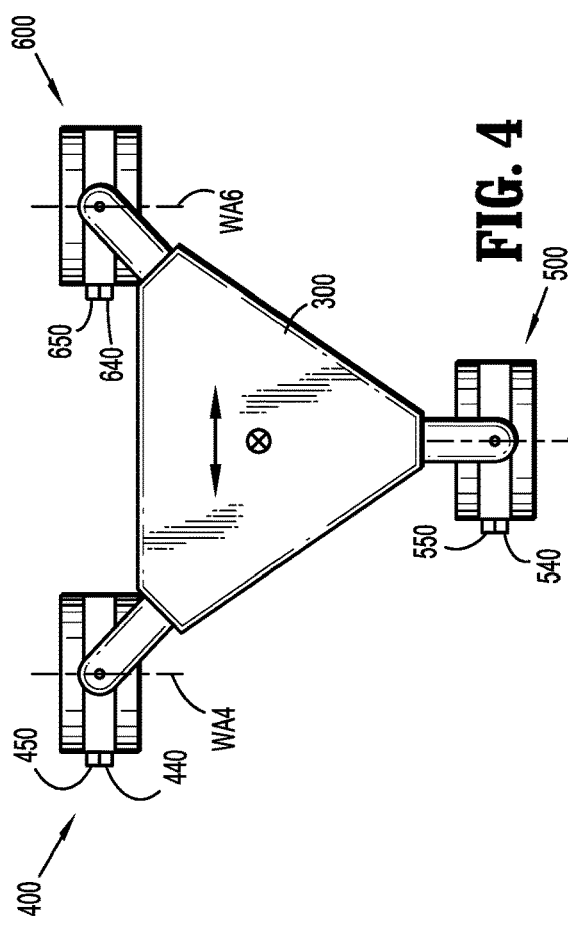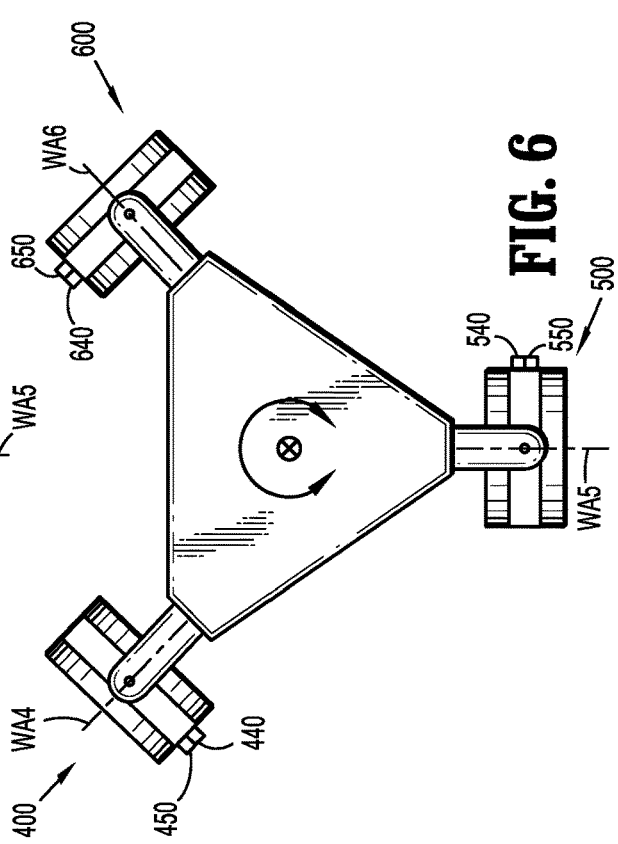

SURGICAL ROBOTIC CART WITH SELECTIVE WHEEL ALIGNMENT

CROSS-REFERENCE TO RELATED APPLICATIONS

This application is a U.S. National Stage Application filed under 35 U.S.C. § 371(a) of International Patent Application Serial No. PCT/US2016/055393, filed Oct. 5, 2016, which claims the benefit of and priority to U.S. Provisional Patent Application Ser. No. 62/239,393, filed Oct. 9, 2015, the entire disclosure of which is incorporated by reference herein.

BACKGROUND

Surgical robotic systems are used in minimally invasive medical procedures because of their increased accuracy and expediency. In surgical robotic systems, a robot arm supports a surgical instrument having an end effector mounted thereto by a wrist assembly. In operation, the robot arm inserts the surgical instrument into or holds a surgical instrument in a small incision via a surgical portal or a natural orifice of a patient to position the end effector at a work site within a patient's body.

Most of the surgical robotic systems on the market are heavy and stationary requiring a pallet jack to be relocated. In some of the more modern surgical robotic systems, the robot arm is supported on a movable surgical robotic cart having a base portion with a set of casters. This is beneficial because the surgical robotic systems can be moved between various rooms as needed without a pallet jack.

However, minimally invasive medical procedures require a high degree of accuracy, precision, and speed, and, therefore, movable surgical robotic systems used for minimally invasive medical procedures need to be precisely immobilized before an operation begins. Accordingly, there is a need to precisely immobilize a surgical robotic cart, and to provide surgical robotic carts with a high degree of movability and maneuverability.

SUMMARY

The present disclosure relates to surgical robotic carts including novel casters and the like for providing improved movability and maneuverability.

In accordance with an embodiment of the present disclosure, a surgical robotic cart assembly includes a base portion configured to support a robotic arm thereon. The cart assembly further includes first, second, and third casters pivotably attached to the base portion along a respective pivot axis to allow the cart assembly to move along a floor without the need for a pallet jack. Each of the first, second, and third casters has a housing and a wheel rotatably coupled thereto. Each of the first, second, and third casters is supported on a rotatable wheel axis, and has a wheel alignment assembly. Each wheel alignment assembly includes a first pedal pivotably coupled to the housing and movable between a first position and a second position, and a second pedal pivotably coupled to the housing and movable between a first position and a second position. The first and second pedals are configured to fix the first, second, or third caster in an orientation. When the first and second pedals of each of the first, second, and third casters is in the first position, each of the first, second, and third casters is free to pivot about its respective pivot axis. When the first pedal of each of the first, second, and third casters is in the second position each of the first, second, and third casters is fixed in an angled orientation relative to its respective pivot axis.

The cart assembly may further be configured such that when the first and second pedals of each of the first, second, and third casters is in the second position, each of the first, second, and third casters may be immobile about its respective wheel axis.

The cart assembly may further be configured such that when the first and second pedals of each of the first, second, and third casters is in the first position, each of the respective first, second, and third casters may be free to rotate 360 degrees about its respective pivot axis and wheel axis, thereby allowing the cart assembly to move in any direction.

The cart assembly may further be configured such that when each of the first, second, and third casters is fixed in an angled orientation relative to its respective pivot axis, each of the first, second, and third casters respective wheel axis may be locked substantially parallel relative to each other allowing the cart assembly to translate.

The cart assembly may further be configured such that when each of the first, second, and third casters is fixed in an angled orientation relative to its respective pivot axis, each of the first, second, and third casters respective wheel axis may be oriented at 120 degrees relative to each other allowing the cart assembly to rotate about a center thereof.

The cart assembly may further be configured such that when the first and second pedals of the first caster is in the second position, and when each of the first and second pedals of the second and third casters is in the second position, the cart assembly may be pivotable about the first caster.

The cart assembly may further include that the angled orientation of each of the first, second, and third casters is pre-selected.

In accordance with another embodiment of the present disclosure, a surgical robotic cart assembly includes a base portion having a robotic arm operatively secured thereon, and three casters pivotably attached to the base portion along a pivot axis. Each of the three casters has a housing, a wheel rotatable on a wheel axis, and a wheel alignment assembly operatively connecting the housing and the wheel. Each wheel alignment assembly includes a first pedal pivotably coupled to the housing and movable between a first position and a second position and a second pedal pivotably coupled to the housing and movable between a first position and a second position. The first and second pedals are configured to fix the respective three casters in an orientation.

The cart assembly may further be configured such that when the first and second pedals of each of the three casters is in the first position, each of the three casters may be free to pivot about its respective pivot axis.

The cart assembly may further be configured such that when the first and second pedals of each of the three casters is in the first position, the respective first, second, and third casters may be free to rotate 360 degrees about its respective pivot axis and wheel axis, thereby allowing the cart assembly to move in any direction.

The cart assembly may further be configured such that when the first pedal of each of the first, second, and third casters is in the second position, each of the first, second, and third casters may be fixed in an angled orientation relative to its respective pivot axis.

The cart assembly may further be configured such that when the first pedal of each of the first, second, and third casters is in the second position, each of the first, second, and third casters respective wheel axis may be locked substantially parallel relative to each other allowing the cart assembly to translate.

The cart assembly may further be configured such that when the first pedal of each of the first, second, and third casters is in the second position, each of the first, second, and third casters respective wheel axis may be locked 120 degrees relative to each other allowing the cart assembly to rotate about a center thereof.

The cart assembly may further be configured such that when the first and second pedals of each of the three casters is in the second position, each of the first, second, and third casters may be immobile about its respective wheel axis.

The cart assembly may further be configured such that when the first and second pedals of the first caster is in the second position, and when each of the first and second pedals of the second and third casters is in the second position, the cart assembly may be pivotable about the first caster.

Further details and aspects of exemplary embodiments of the present disclosure are described in more detail below with reference to the appended figures.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of exemplary embodiment(s) given below, serve to explain the principles of the disclosure, wherein:

FIG. 3 is a bottom, plan view of the surgical robotic cart assembly of FIG. 1, illustrating each immobilization assembly of the plurality of casters in an unlocked position;

FIG. 4 is a bottom, plan view of the surgical robotic cart assembly of FIG. 1, illustrating each immobilization assembly of the plurality of casters locked in a first orientation;

FIG. 5 is a bottom, plan view of the surgical robotic cart assembly of FIG. 1, illustrating each immobilization assembly of the plurality of casters locked in a second orientation;

FIG. 6 is a bottom, plan view of the surgical robotic cart assembly of FIG. 1, illustrating each immobilization assembly of the plurality of casters locked in a third orientation.

DETAILED DESCRIPTION

Figure 1:
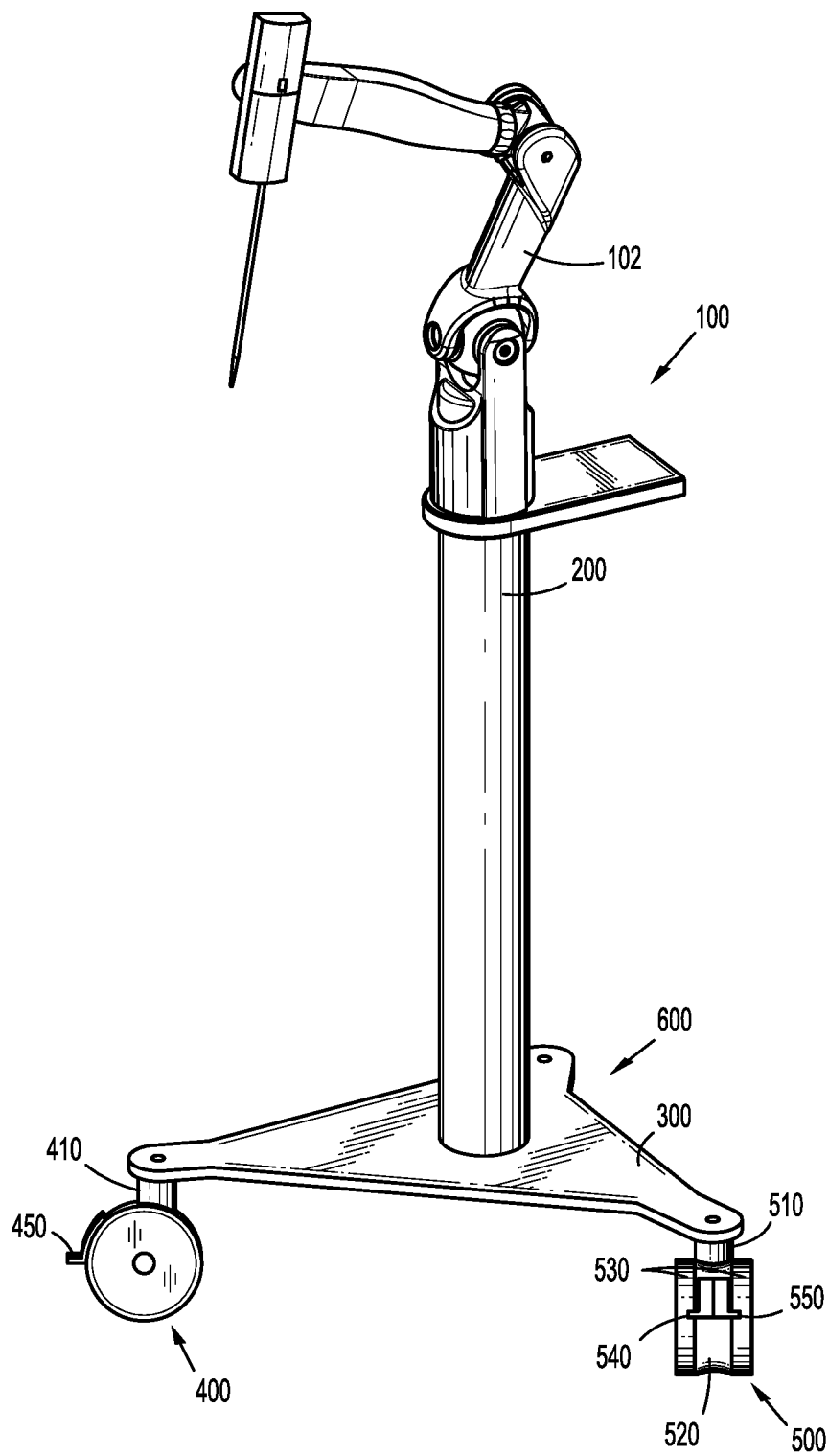
FIG. 1 is a perspective view of a surgical robotic cart assembly in accordance with the present disclosure.

Embodiments of the present disclosure are described in detail with reference to the drawings, in which like reference numerals designate identical or corresponding elements in each of the several views.

Figure 2:
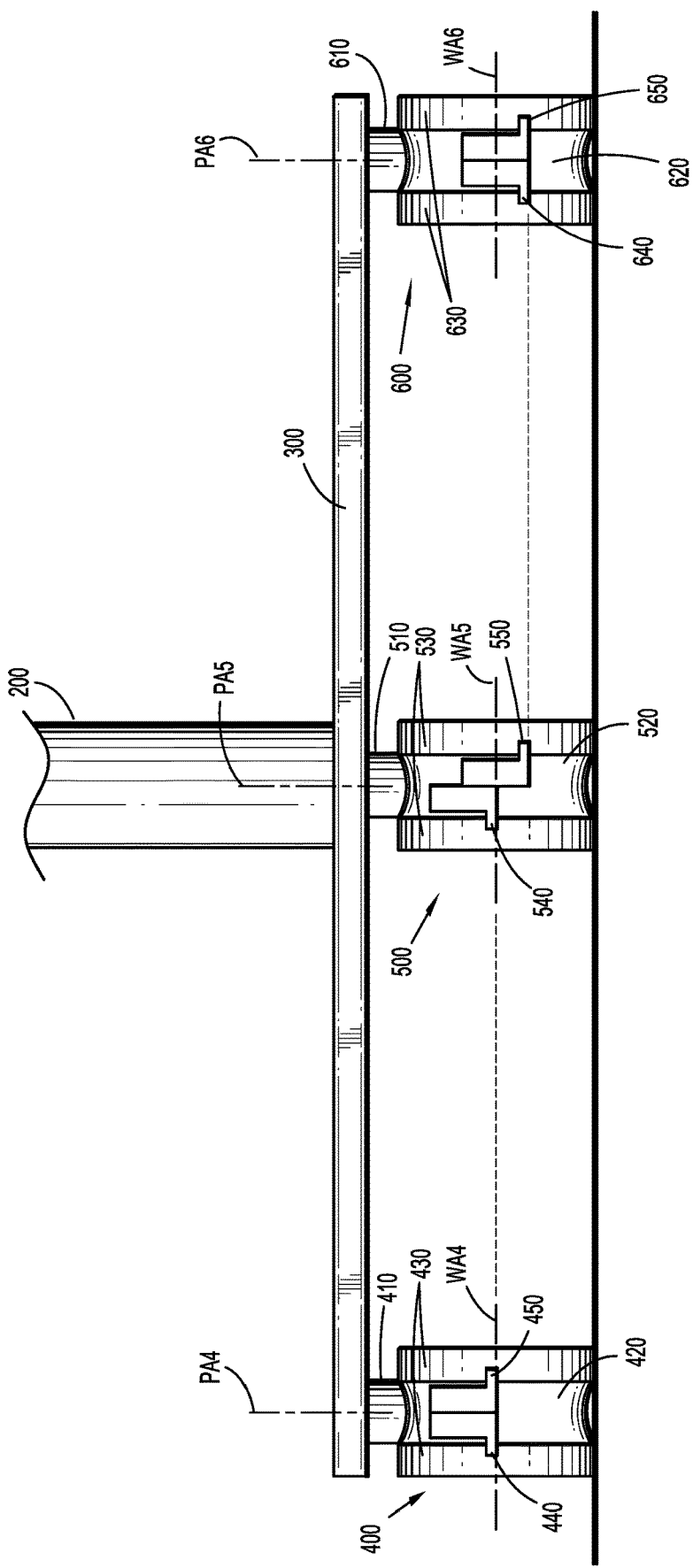
FIG. 2 is a front, elevational view of the surgical robotic cart assembly of FIG. 1 illustrating a base portion and a plurality of casters each having an immobilization assembly.

With reference to FIGS. 1 and 2, one exemplary embodiment of a surgical robotic cart assembly configured for use in accordance with the present disclosure is generally identified as 100, although it is also envisioned that the aspects and features of the present disclosure be similarly incorporated into any suitable surgical robotic cart assembly. Surgical robotic cart assembly 100 generally includes a robotic arm 102, a vertical column 200, and a base portion 300. Base portion 300 includes a plurality of casters 400, 500, and 600 coupled thereto. Each of the casters 400, 500, and 600 is configured to swivel about a respective pivot axis, and configured to allow surgical robotic cart assembly 100 to move, or to inhibit movement of surgical robotic cart assembly 100. Each of the casters 400, 500, and 600 includes a respective housing 410, 510, and 610, where each of the respective housings 410, 510, and 610 is pivotably attached to the base portion 300, and defines a respective pivot or swivel axis "PA4," "PA5," and "PA6".

Casters 400, 500, and 600 further include a set of wheels 430, 530, and 630 rotatably coupled to each of the respective housings 420, 520, and 620. Although a set of wheels is discussed, any suitable number of wheels may be used. Wheels 430, 530, and 630 each define a respective wheel axis through its center, shown as "WA4," "WA5," and "WA6".

Casters 400, 500, and 600 each further include an immobilization system having a respective first pedal 440, 540, and 640, and a respective second pedal 450, 550, and 650. First and second pedals 440, 540, 640, 450, 550, and 650 are pivotably coupled to respective housings 420, 520, and 620 and operatively connected to respective wheels 430, 530, and 630. Each respective first pedal 440, 540, and 640 and second pedal 450, 550, and 650 is configured to move between a first position and a second position.

Each of the first pedals 440, 540, and 640 moves the respective casters 400, 500, and 600 between an unlocked orientation when the respective first pedals 440, 540, and 640 are in the first position and a first locked orientation when the respective first pedals are in the second position. Each of the second pedals 450, 550, and 650 moves the respective casters 400, 500, and 600 between an unlocked orientation when the respective second pedals 440, 540, and 640 are in the first position and a second locked orientation when the respective second pedals 440, 540, and 640 are in the second position With reference to FIG. 2, first pedals 440 and 540 of casters 400, 500 are shown disposed in the first position, while pedal 640 of caster 600 is disposed in the second position.

With continuing reference to FIG. 2, second pedal 450 is shown in the first position while second pedals 550 and 650 are in the second position.

In operation, each of the respective casters 400, 500, and 600 may be in one of four different possible orientations which are listed below:

Orientation I. When the first pedal is in the first position and second pedal in the first position, the wheels of the caster is free to rotate.

Orientation II. When the first pedal is in the first position and the second pedal is in the second position, the caster is fixed in a first angled orientation.

Orientation III. When the first pedal is in the second position and the second pedal is in the first position, the caster is fixed in a second angled orientation that is different from the first angled orientation.

Orientation IV. When the first pedal is in the second position and the second pedal is in the second position, the wheel of the caster is locked against any rotation thereof.

The first and second angled orientations of the casters may be pre-determined. For example, with reference to FIG. 2, caster 400 is in Orientation I, caster 500 is in Orientation II, and caster 600 is in Orientation IV. An operator may select an orientation of each respective caster 400, 500, and 600 in order to vary a mode of movement of surgical robotic cart assembly 100.

Turning to FIGS. 3-5, each of the casters 400, 500, and 600 are in a selected orientation. As shown in FIG. 3, each of the casters 400, 500, and 600 are in Orientation I, thereby allowing surgical robotic cart assembly 100 complete maneuverability, e.g., to rotate about its center, translate longitudinally, and translate laterally or any combinations thereof. As shown in FIG. 4, each of the casters 400, 500, and 600 are in Orientation II. In Orientation II, with each of the respective wheel axes "WA4," "WA5," and "WA6" parallel relative to each other, the surgical robotic cart assembly 100 may translate in a single lateral direction. In this configuration, it is contemplated that surgical robotic cart assembly 100 may be moved along a side of a surgical table. Alternatively, as show in FIG. 5, when each of the casters 400, 500, and 600 are in Orientation II, and each of the respective wheel axes "WA4," "WA5," and "WA6" are parallel relative to each other (with two wheel axes disposed on a common axis), the surgical robotic cart assembly 100 may translate in a longitudinal direction. In this configuration, it is contemplated that surgical robotic cart assembly 100 may be moved toward or away from a surgical table.

With reference to FIG. 6, each of the casters 400, 500, and 600 are in Orientation III. In Orientation III, each of the respective wheel axes "WA4," "WA5," and "WA6," is disposed at a 120 degree angle relative to one another which allows surgical robotic cart assembly 100 to rotate about a center "C" thereof.

Figure 7:
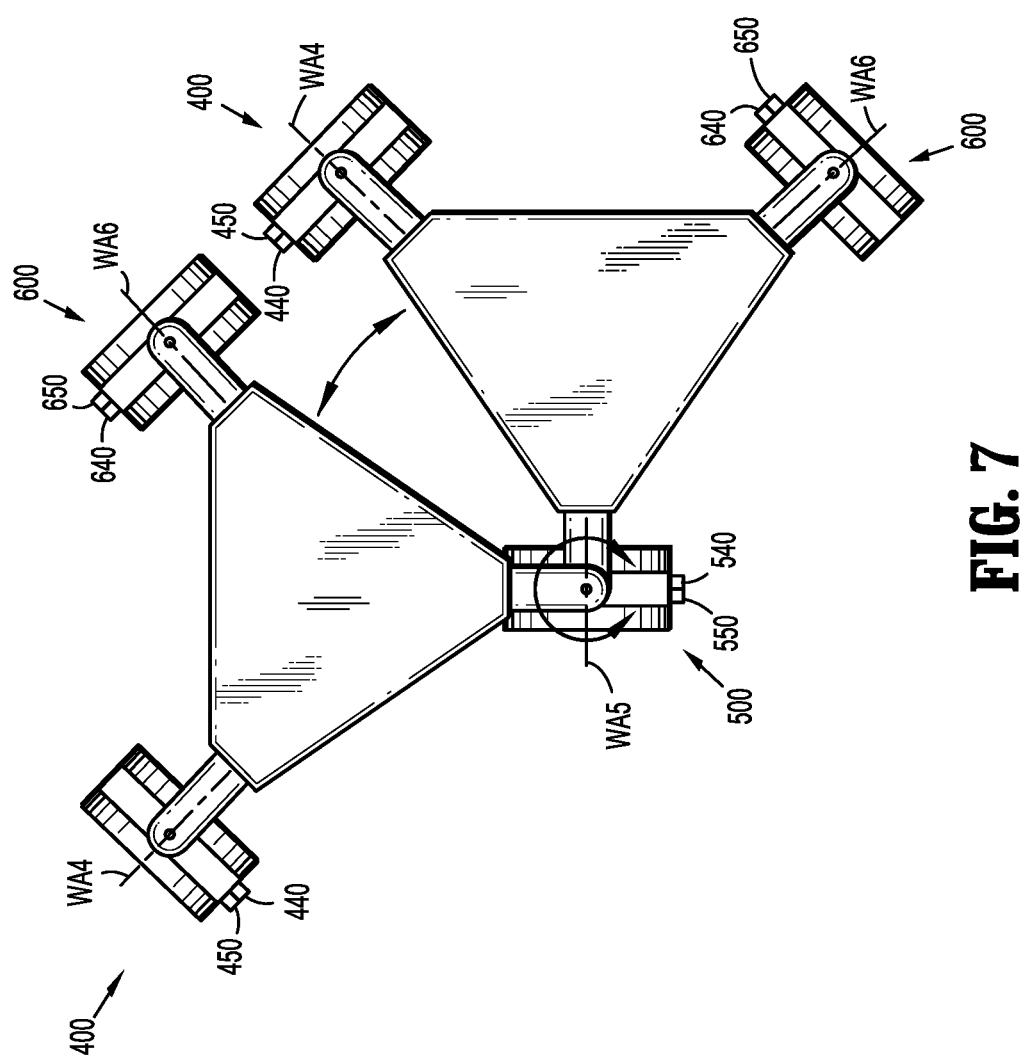
FIG. 7 is a bottom, plan view of the surgical robotic cart assembly of FIG. 1, illustrating two out of three immobilization assemblies of the plurality of casters locked in the third orientation.

Now turning to FIG. 7, surgical robotic cart assembly 100 has casters 400 and 600 in Orientation III while caster 500 is in Orientation IV. Casters 400 and 600 are at a fixed orientation such that their respective wheel axes "WA4" and "WA6" are positioned at a 120 degree angle relative to each other, and unlocked caster 500 is free to rotate. In use, as so configured, surgical robotic cart assembly 100 freely pivots about pivot axis "PA5" of unlocked caster 500.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the claimed invention. Therefore, the above description should not be construed as limiting, but merely as exemplifications of particular embodiments. Those skilled in the art will envision other modifications within the scope and spirit of the claims appended hereto.

What is claimed is:

1. A surgical robotic cart assembly, comprising:
   a base portion having a robotic arm operatively secured thereon; and
   first, second, and third casters pivotably attached to the base portion along a respective pivot axis, each of the first, second, and third casters having a housing, a wheel rotatably coupled to the housing and defining a wheel rotation axis, and a wheel alignment assembly, each wheel alignment assembly including:
   a first pedal pivotably coupled to the housing and movable between a first position and a second position; and
   a second pedal pivotably coupled to the housing and movable between a first position and a second position, wherein the first and second pedals are configured such that selective and independent actuation thereof results in independent fixing of each of the first, second, and third casters in a selected predetermined orientation about their respective pivot axis and independent prevention of rotation of each of the first, second and third casters about their respective wheel rotation axis,
   wherein when the first and second pedals of each of the first, second, and third casters is in the first position, each of the first, second, and third casters is free to pivot about their respective pivot axis, and is free to rotate about their respective wheel rotation axis;
   wherein when the first pedal of each of the first, second, and third casters is in the second position each of the first, second, and third casters is fixed in a first orientation about the respective pivot axis thereof;
   wherein when the second pedal of each of the first, second, and third casters is in the second position each of the first, second, and third casters is fixed in a second orientation about the respective pivot axis thereof, the second orientation being different than the first orientation; and
   wherein the surgical robotic cart assembly includes a configuration where:
   the first pedal of the first caster is in the second position and the second pedal of the first caster is in the second position to prevent the first caster from rotating about the wheel rotation axis thereof, and permit the first caster to pivot about the pivot axis thereof; and
   the first pedal of each of the second caster and the third caster is in the second position, and the second pedal of each of the second caster and the third caster is in the first position, to orient the wheel rotation axis of the second caster and the third caster at 120° relative to one another,
   whereby the surgical robotic cart assembly, as a whole, pivots about the pivot axis of the first caster.

2. The surgical robotic cart assembly of claim 1, wherein when the first and second pedals of each of the first, second, and third casters is in the second position, each of the first, second, and third casters is immobile about the respective wheel rotation axis thereof.

3. The surgical robotic cart assembly of claim 2, wherein when each of the first, second, and third casters is fixed in an orientation relative to the respective pivot axis thereof, each of the first, second, and third casters respective wheel rotation axis is locked substantially parallel relative to each other allowing the cart assembly to translate.

4. The surgical robotic cart assembly of claim 2, wherein when each of the first, second, and third casters is fixed in an orientation relative to the respective pivot axis thereof, each of the first, second, and third casters respective wheel rotation axis is oriented at 120 degrees relative to each other allowing the cart assembly to rotate about a center thereof.

5. The surgical robotic cart assembly of claim 4, wherein when the first and second pedals of the first caster is in the second position, and when each of the first and second pedals of the second and third casters is in the second position, the cart assembly is pivotable about the first caster.

6. The surgical robotic cart assembly of claim 1, wherein when the first and second pedals of each of the first, second, and third casters is in the first position, each of the respective first, second, and third casters is free to rotate 360 degrees about the respective pivot axis and wheel rotation axis thereof, thereby allowing the cart assembly to move in any direction.

7. The surgical robotic cart assembly of claim 1, wherein the fixed orientation of the first, second and third casters is pre-selected.

8. The surgical robotic cart assembly of claim 1, wherein the first, second, and third casters are arranged in a triangular configuration.

9. The surgical robotic cart assembly of claim 8, wherein the cart assembly includes only the first, second, and third casters.

10. A surgical robotic cart assembly, comprising:
a base portion having a robotic arm operatively secured thereon; and
three casters pivotably attached to the base portion along a pivot axis, each of the three casters having a housing, a wheel rotatable on a wheel axis, and a wheel alignment assembly operatively connecting the housing and the wheel, each wheel alignment assembly including:
a first pedal pivotably coupled to the housing and movable between a first position and a second position; and
a second pedal pivotably coupled to the housing and movable between a first position and a second position, wherein the first and second pedals are configured such that selective and independent actuation thereof results in independent fixing of each of the first, second, and third casters in a selected predetermined orientation about the respective pivot axis and independent prevention of rotation of each of the first, second and third casters about a respective wheel rotation axis,
wherein the surgical robotic cart assembly includes a configuration where:
the first pedal of the first caster is in the second position and the second pedal of the first caster is in the second position to prevent the first caster from rotating about the wheel rotation axis thereof, and permit the first caster to pivot about the pivot axis thereof; and
the first pedal of each of the second caster and the third caster is in the second position, and the second pedal of each of the second caster and the third caster is in the first position, to orient the wheel rotation axis of the second caster and the third caster at 120° relative to one another,
whereby the surgical robotic cart assembly, as a whole, pivots about the pivot axis of the first caster.

11. The surgical robotic cart assembly of claim 10, wherein when the first and second pedals of each of the three casters is in the first position, each of the three casters is free to pivot about a respective pivot axis thereof.

12. The surgical robotic cart assembly of claim 11, wherein when the first and second pedals of each of the three casters is in the first position, the respective first, second, and third casters is free to rotate 360 degrees about the respective pivot axis and wheel axis thereof thereby allowing the cart assembly to move in any direction.

13. The surgical robotic cart assembly of claim 11, wherein when the first pedal of each of the first, second, and third casters is in the second position each of the first, second, and third casters is fixed in an orientation relative to the respective pivot axis thereof.

14. The surgical robotic cart assembly of claim 13, wherein when the first pedal of each of the first, second, and third casters is in the second position, each of the first, second, and third casters respective wheel axis is locked substantially parallel relative to each other allowing the cart assembly to translate.

15. The surgical robotic cart assembly of claim 13, wherein when the first pedal of each of the first, second, and third casters is in the second position, each of the first, second, and third casters respective wheel axis is locked at a 120 degree angle relative to each other allowing the cart assembly to rotate about a center thereof.

16. The surgical robotic cart assembly of claim 15, wherein when the first and second pedals of each of the three casters is in the second position, each of the first, second, and third casters is immobile about the respective wheel axis thereof.

17. The surgical robotic cart assembly of claim 16, wherein when the first and second pedals of the first caster is in the second position, and when each of the first and second pedals of the second and third casters is in the second position, the cart assembly is pivotable about the first caster.

18. The surgical robotic cart assembly of claim 10, wherein the first, second, and third casters are arranged in a triangular configuration.

19. The surgical robotic cart assembly of claim 18, wherein the cart assembly includes only the first, second, and third casters.

* * * * *